US00PP36861P2

(12) United States Plant Patent
Hansoti

(10) Patent No.: US PP36,861 P2
(45) Date of Patent: Jul. 22, 2025

(54) ***SANSEVIERIA* PLANT NAMED 'Hansoti58'**

(50) Latin Name: *Sansevieria trifasciata*
Varietal Denomination: Hansoti58

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,668

(22) Filed: Dec. 23, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./382
See application file for complete search history.

*Primary Examiner* — Susan McCormick Ewoldt

(57) ABSTRACT

A new and distinct cultivar of *Sansevieria* plant named 'HANSOTI58' is disclosed, characterized by bright cream variegated foliage with broad central lighter grey-green band along the length of the leaf, veiled by a creamy overlayer and a base cream background color of the leaf between the border bands and the central band. Foliage has a prominent, dark grey-green marginal band, 2 to 15 mm wide but occasionally up to 25 mm wide distinguishes this invention from its parent 'Ghost' and adds significant photosynthetic capacity and so strength and growth speed to this new cultivar compared to 'Ghost'. The new cultivar can be classified in the Compact *Sansevieria* Group. The new variety is a *Sansevieria*, typically produced as an ornamental plant.

10 Drawing Sheets

Latin name of the genus and species: *Sansevieria trifasciata.*
Variety denomination: 'HANSOTI58'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI58'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI58' was discovered and selected by the inventor, Ashish Hansoti, as a number of aberrant side shoots within a planting of *Sansevieria trifasciata* 'Ghost' (an unpatented cultivar selected and grown by the Inventor) in early 2019, at a nursery in Village Vangani, District Thane, Maharashtra State in Western India. Several shoots with the aberrant or new variegation pattern were isolated and planted individually and further selection for the desired characteristics was done till we got stable plants of the correct phenotype.

Asexual reproduction in good numbers of the new, relatively stabilised *Sansevieria* cultivar 'HANSOTI58' by vegetative cuttings was started in mid to late 2020 at Village Asle, District Satara, Maharashtra State in Western India and it was seen that, after a few more rounds of discarding of off-types, the distinctive combination of characteristics of the new cultivar reproduced true to type as long as the propagation was done through side shoots (basal suckers) originating from the base of the parent plant. Thus, it can be said that the new cultivar reproduces true to type through side shoots (basal suckers)

BRIEF SUMMARY OF THE INVENTION

The following traits have been repeatedly observed and are determined to be unique characteristics of 'HANSOTI58', which in combination distinguish this *Sansevieria* as a new and distinct cultivar:

1. A prominent, dark grey-green marginal band, 2 to 15 mm wide but occasionally up to 25 mm wide distinguishes this invention from its parent 'Ghost' and adds significant photosynthetic capacity and so strength and growth speed to this new cultivar compared to 'Ghost'.
2. Bright cream variegated foliage with broad central lighter grey-green band along the length of the leaf, veiled by a creamy overlayer and a base cream background color of the leaf between the border bands and the central band.

The new variety 'HANSOTI58' is considered a variety of *Sansevieria* in the group denominated as the "Compact *Sansevieria* Group". The new variety presents an average of 7 to 9 leaves per plant when it reaches its saleable size (between 3 to 4 months from rooted liner). The new variety has a semi-erect growth habit and the entire plant can reach a height ranging between 20 and 25 cm. The leaves are of medium width (5 to 7 cm) measured at the widest part of the mature leaf under good growing conditions) and broad-lanceolate with a firm, waxy texture. The blades are thick or fleshy and slightly wavy. This variety also has an inverted triangle shape like most *Sansevieria* of the Compact Group.

The new variety is moderately drought tolerant and adapts well to conditions of bright light and semi-shade (exterior and interior).

The leaves show a bright variegated coloration, with a wide central band of light grey-green and broad border bands of dark grey-green along both leaf edges. A creamy layer of tissue covers or overlays the central green band to varying degrees so that this central band appears as a light greyish-green.

The broad central band shows grey green colorations overlaid with a layer of cream and an overall effect ranging from near Greyed-Green 188C or 188D to 189C or 189D.

However, due to extreme variability of shade and the overlying creamy coloration it is difficult to pinpoint the exact shade.

Each leaf has a marginal band that is darker grey green which varies in width from just 2 mm to 15 mm. This marginal band often has some creamy incursions into it and so appears "Painted", an attribute that enhances the beauty of the leaf of this new invention. Color of this band starts out light grey green but in a mature leaf the band is darker, near Green 137B to 138B. The base creamy color, between the two bands, is near Yellow 4D.

Superimposed on the above are very faint and barely visible lighter horizontal cross-banding (typical of broad leaved *Sansevieria* including 'Ghost') but only over the central band and almost unnoticeable across the creamy base color. The broad bands along the edge, even though dark grey-green, show no hint of these transverse bands.

Backside of the leaves is essentially the same coloring and pattern as the front with a wide central grey-green band somewhat lighter than in front and the darker, prominent grey-green marginal bands. However, the marginal dark green bands are generally a lot narrower at the back of the leaf, typically only 2 to 10 mm wide even where the same band on the front is much wider.

Attached color pictures are a better guide to the overall variegation and coloration.

PARENTAL COMPARISON

Plants of the new *Sansevieria* 'HANSOTI58' are similar to plants of the parental cultivar, however, 'HANSOTI58' differs in the characteristics described in Table I.

In brief, the new 'Hansoti58' is basically overall similar to the parent cultivar 'Ghost' but with additional broad prominent grey-green borders along both leaf sides, giving better visual definition to the leaf and a stronger plant due to greater photosynthetic area. The central creamy-green band is broader.

TABLE I

Comparison of New and Parental varieties

| | Characteristic | Parent *S. trifasciata* 'Ghost' | New cv 'Hansoti58' |
|---|---|---|---|
| 1. | Overall Color | Bright, overall creamy look with central broad band of light green and streaks and bands of variable width and bright green color markings along edges. | Less creamy overall look because the prominent dark grey-green bands along leaf edges that encroach into the creamy areas. |
| 2. | Border | A well-defined, dark green 1-2 mm edge and inside that a very variable, light, stippled, discontinuous band of bright green to light grey green - typically around 10 mm wide but may be entirely absent or up to 25 mm wide. | Dark grey-green, prominent border, 2 to 15 mm or more wide, along both sides of leaf. This green band is frequently invaded in places by cream, giving a 'painted' or 'feathered' look, especially in younger leaves. |
| 3. | Leaf Center | Broad, diffuse green band overlaid with cream and surrounded by broad area of bright cream. | Central diffuse green band is broader, lighter, overlaid with more cream. Surrounding cream zone is narrow, being covered to large extent by the dark green edge band. |
| 4. | Vigor | Slower than most *Sansevieria trifasciata* cultivars | More vigorous than parent due to additional chlorophyll in broad, dark border band. |

The variety 'Ghost' gave rise to the variety 'Hansoti58'. 'Ghost' shows less vigor than 'Hansoti58', typically has fewer leaves per plant (4-5), with a somewhat narrower leaf with an average leaf width of 6 cm (measured in the middle of the mature leaf.) The growth habit is semi-erect and presents wide leaves supported in a rosette. The entire plant can reach a size from 20-30 cm. The plant has, as for 'Hansoti58', an inverted triangle shape. The leaves are broad lanceolate with a waxy texture.

The parent 'Ghost' presents as an overall cream colored plant with bands and lines of bright green along the sides of the leaf and a broad central band of very light green overlaid with cream (the green tissue is deeper in the leaf). On the side of each leaf there are bands, shreds and wisps of green color, highly variable in width (from almost absent to 25 mm or even more wide) and in color (ranging from a light pastel green to light grey-green).

In comparison, Hansoti58 presents as a somewhat less creamy plant: the central green central band with greyish overlay is wider and the marginal bands (2 to 15 mm wide), prominent dark, grey-green also encroach on the cream area. These two together restrict the cream area compared to the same in 'Ghost'. Each leaf has the thin 1-2 mm dark green edge and then inside that the prominent dark grey-green band into which lines of cream sometimes enter, giving the leaf a "feathered" or "Painted" look.

This overall difference in the amount of green in the leaf gives a distinctly different look from the parent while also increasing the cultivars growth speed and its overall vigor.

COMMERCIAL COMPARATOR

Plants of the new *Sansevieria* 'HANSOTI58' are similar to the commercial variety *Sansevieria* 'Futura Superba', unpatented. However, 'HANSOTI58' differs in the characteristics described in Table II.

TABLE II

Comparison of well-known variety 'Futura Superba' & the new variety 'Hansoti58'

| | Characteristic | Comparable Cultivar *S. trifasciata* 'Futura Superba' | New cv 'Hansoti58' |
|---|---|---|---|
| 1. | Leaf size | Up to 30 cm or longer | 20 to 25 cm long |
| 2. | Phyllotaxy | Leaves held upright or almost vertical | Leaves held somewhat reflexed |

TABLE II-continued

| Comparison of well-known variety 'Futura Superba' & the new variety 'Hansoti58' | | | |
|---|---|---|---|
| | Characteristic | Comparable Cultivar *S. trifasciata* 'Futura Superba' | New cv 'Hansoti58' |
| 3. | Variegation Pattern | Overall Dark Green leaves with prominent transverse markings and a creamy yellow border band. | Overall Creamy leaves with broad central grey green band AND darker grey green border bands. |
| 4. | Border variegation | 2 to 15 mm wide creamy yellow band with subdued transverse banding. | 2 to 15 mm or wider dark grey-green band with no transverse banding. |
| 5. | Central Variegation | Grey-Green leaf with no central variegation, but with prominent transverse banding in leaf central area. | Broad grey green band with an overlay of cream, very subdued transverse banding. |

BRIEF DESCRIPTION OF THE PHOTOGRAPHS

The accompanying photographs illustrate the overall appearance of the new *Sansevieria* cultivar 'HANSOTI58' showing the colors as true as is reasonably possible with colored reproductions of this type. Colors in the photographs may differ slightly from the color value cited in the detailed botanical description which accurately describe the color of 'HANSOTI58'.

These pictures illustrate the plant form which is the unique characteristic of 'HANSOTI58' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

FIG. 1, FIG. 2 and FIG. 3 show a saleable size plant of *Sansevieria* 'Hansoti58' in a 12 cm diameter pot from various angles. The photos illustrate top as well as bottom of leaves and the leaf arrangement.

FIG. 4, FIG. 5 and FIG. 6: Show different views of a tray of 'Hansoti58' with 8 plants in 12 cm pots showing uniformity across multiple plants.

FIG. 7 illustrates the three cultivars cited in this patent application pictured together for easy comparison. The new cultivar 'Hansoti58' (Top) showing an overall cream coloration but with darker grey green edge bands. The unpatented parent cultivar 'Ghost' (Bottom Left) showing creamier overall colour and indistinct bright green border coloration. Finally, the old, standard cultivar 'Futura Superba' (Bottom Right) representing the classic "Compact *Sansevieria* Group" showing bigger, broader, more robust leaves and fewer leaves.

DETAILED BOTANICAL DESCRIPTION

Figure 1:
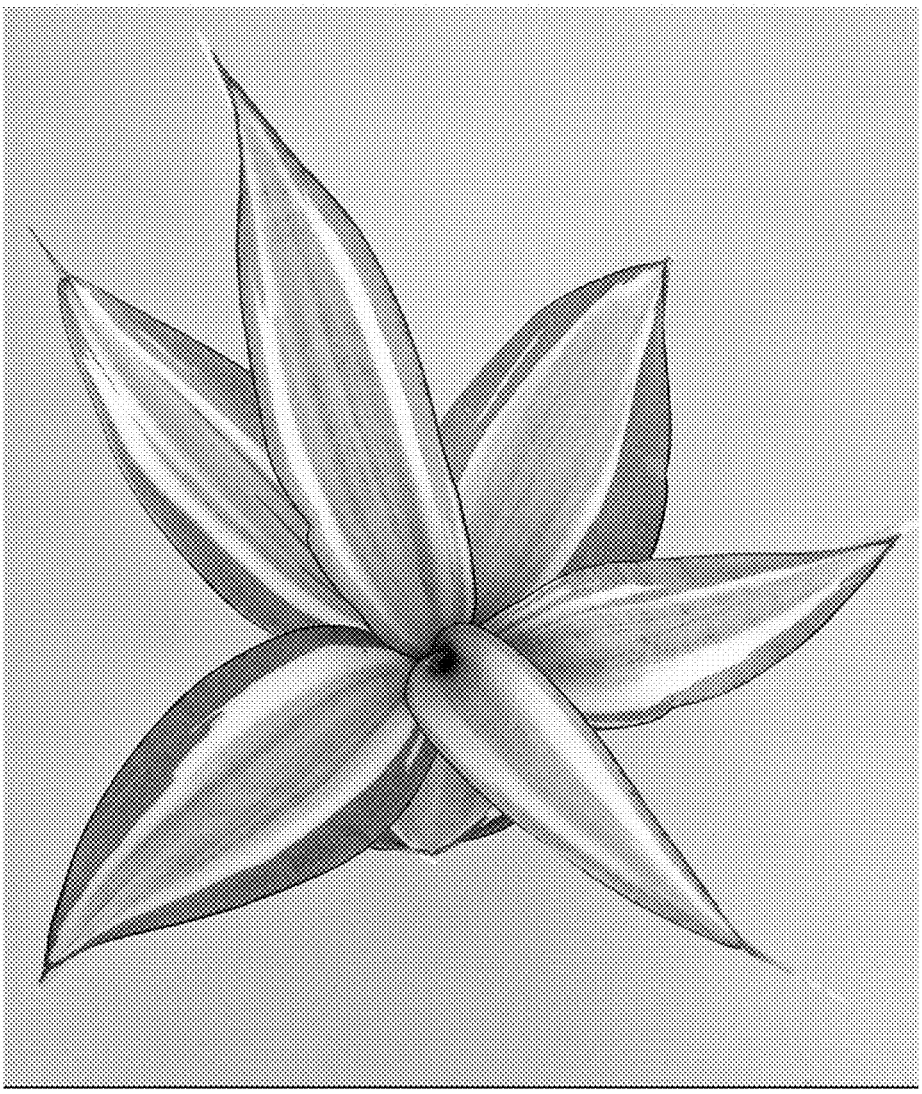
Figure 2:
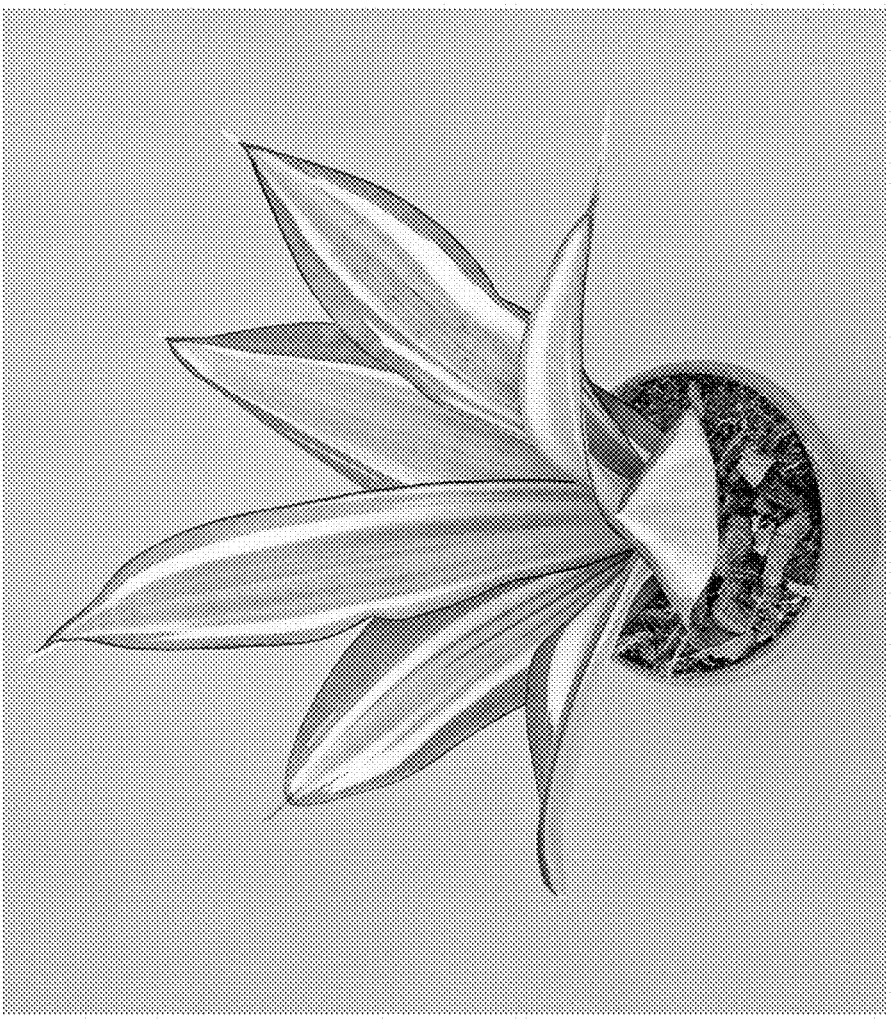
Figure 3:
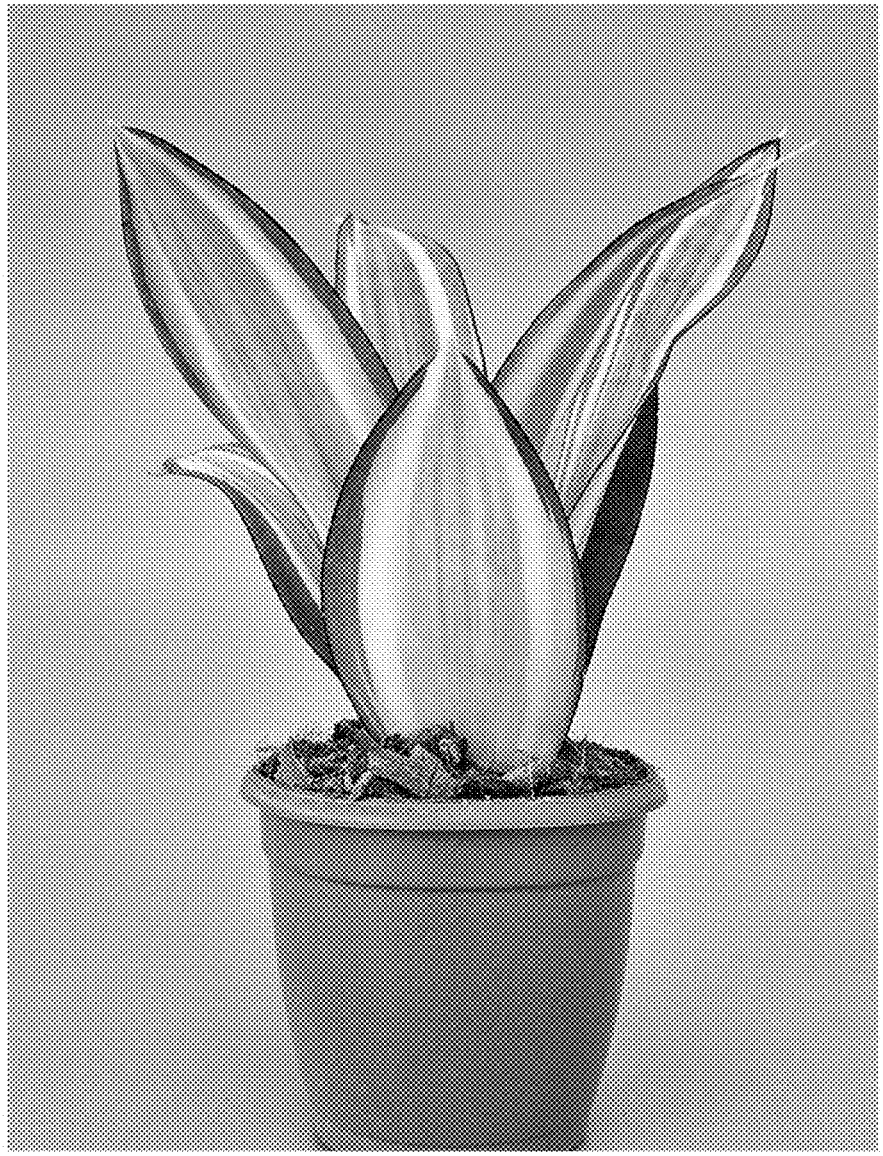
Figure 4:
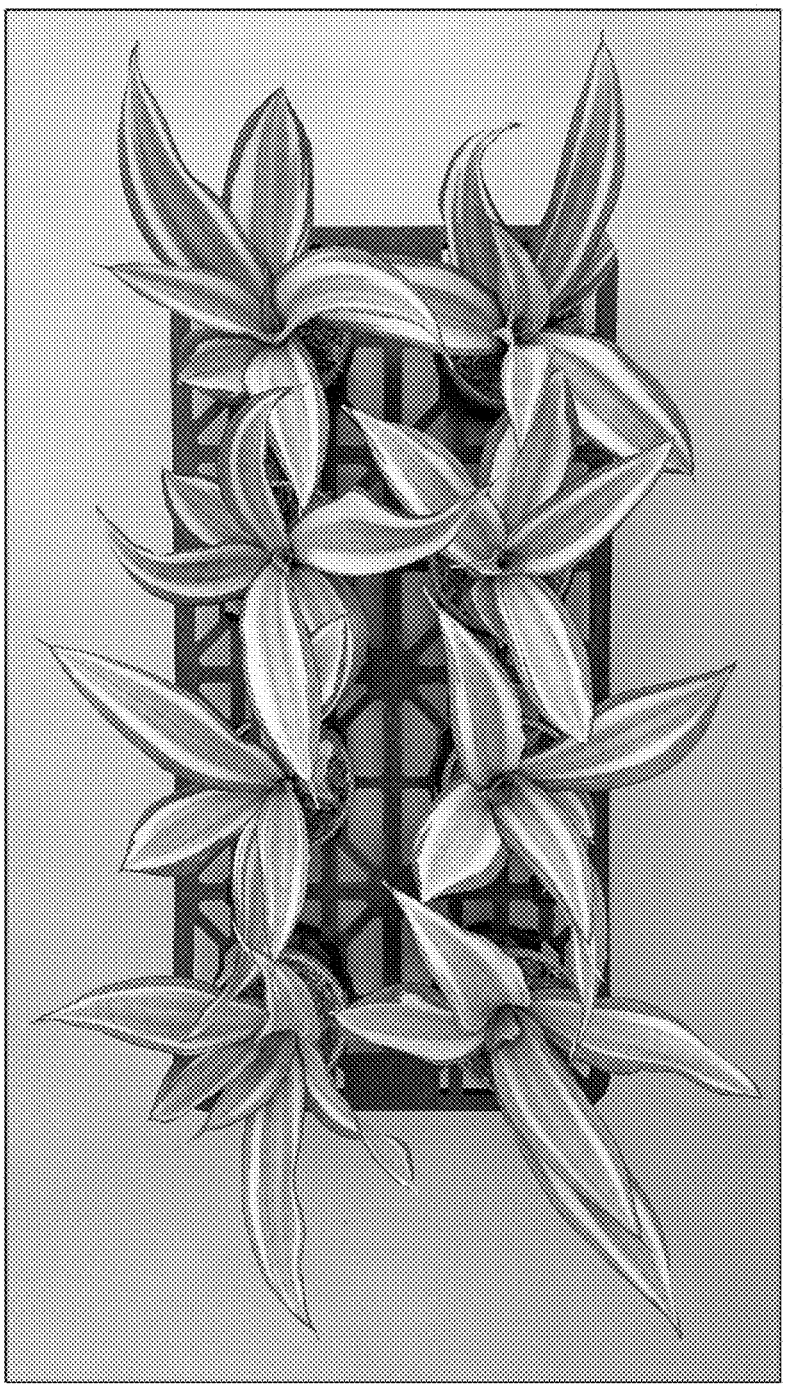
Figure 5:
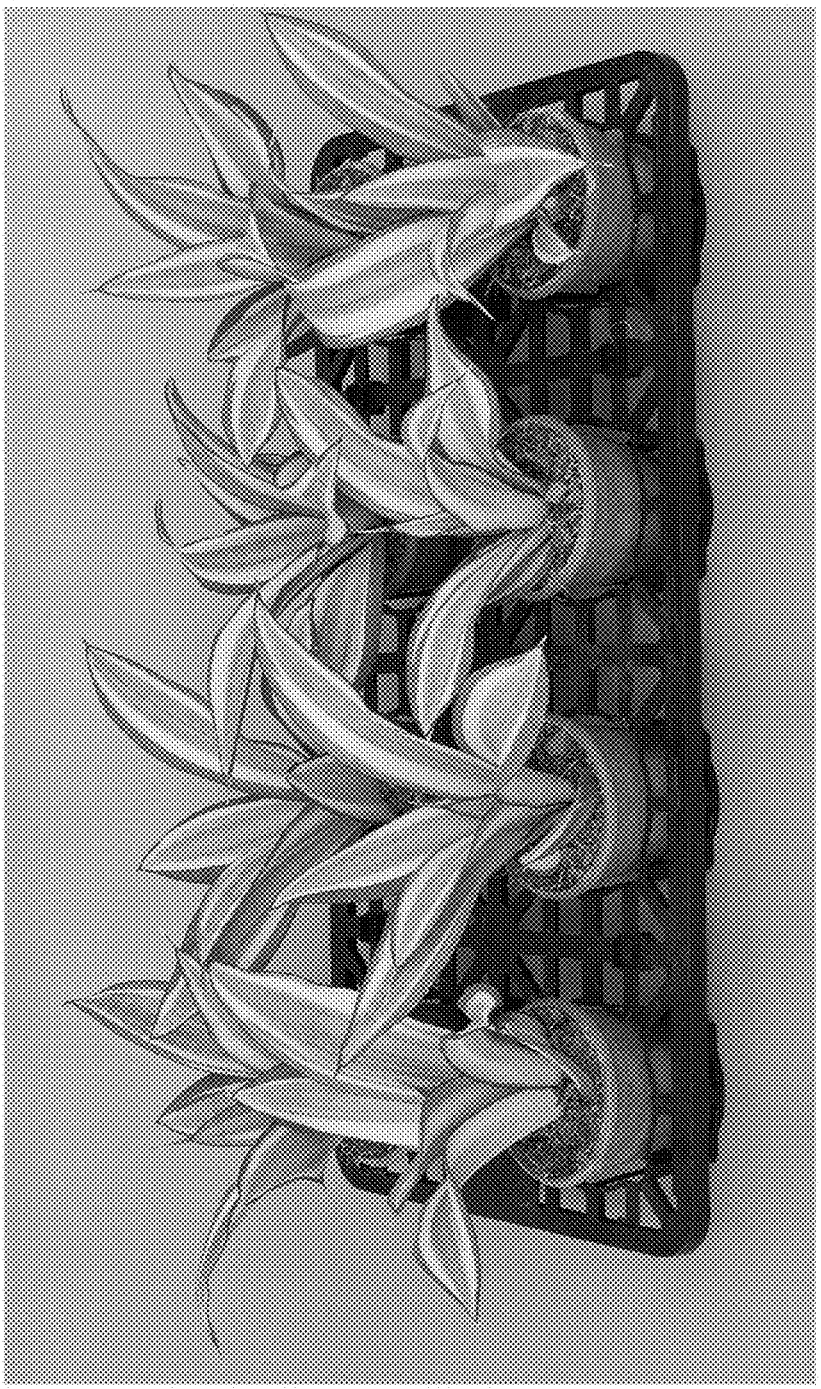
Figure 6:
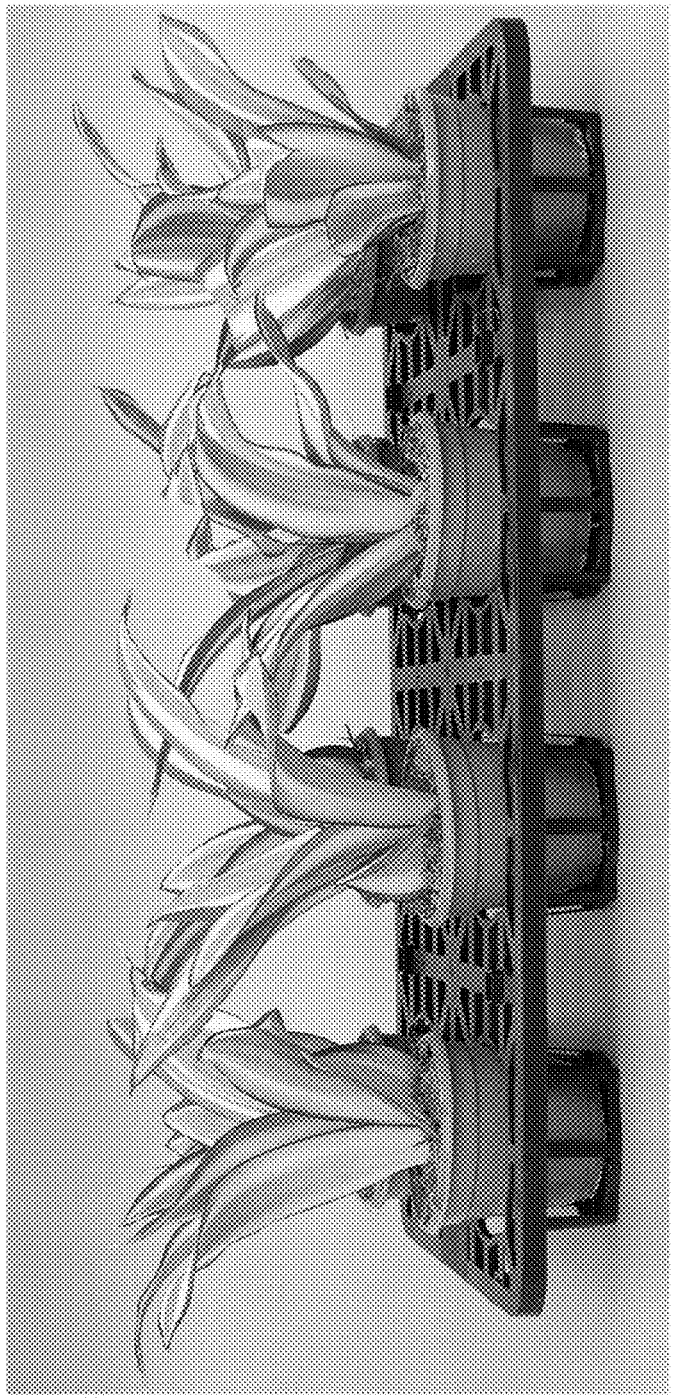
Figure 7:
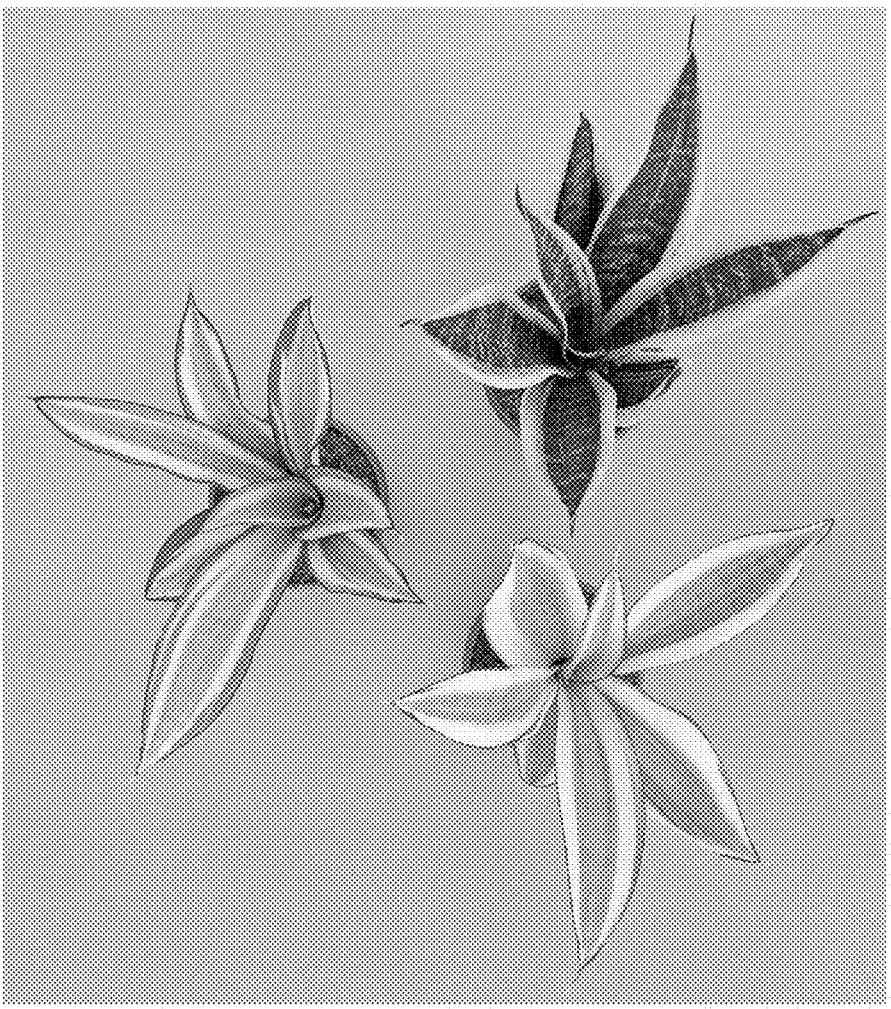
Figure 8:
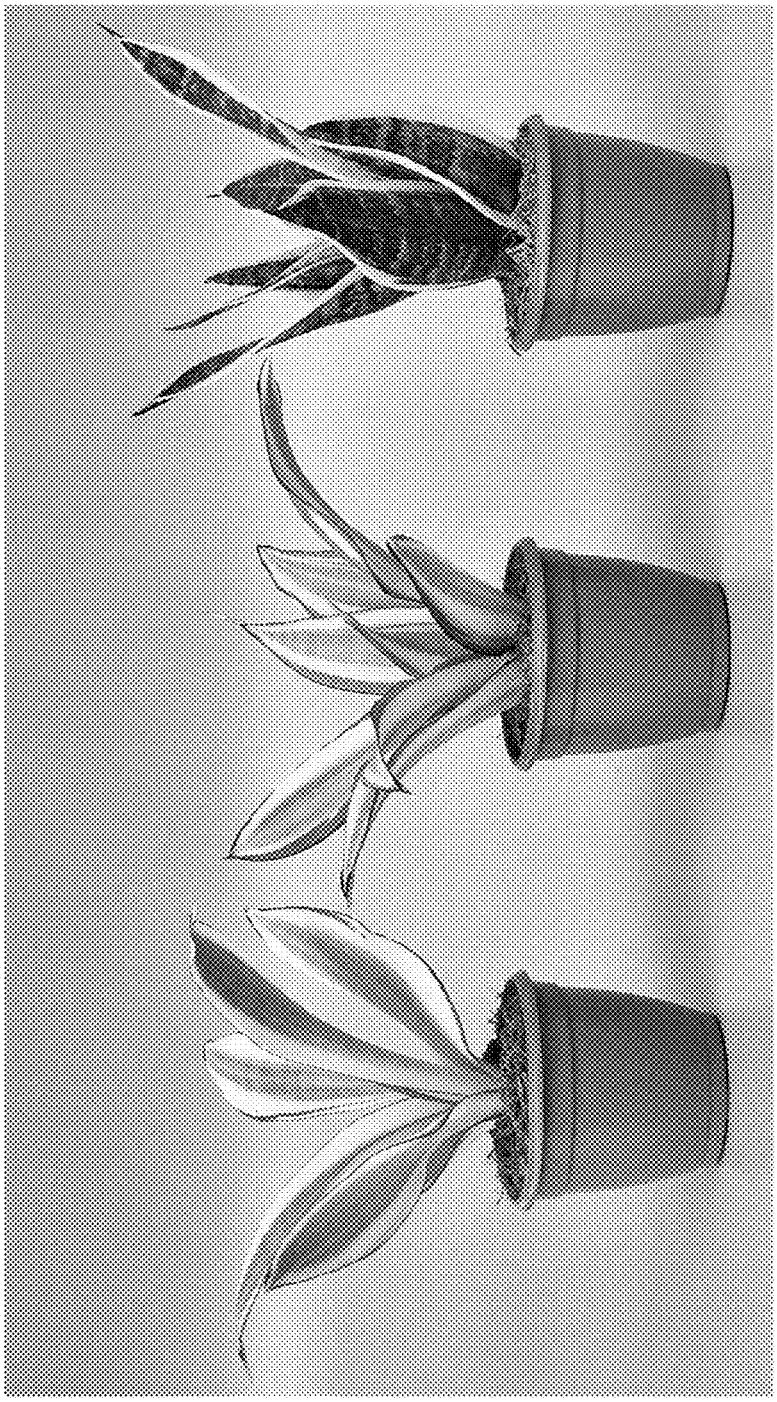
FIG. 8 illustrates the same cultivars from FIG. 7 from a side view.
Figure 9:
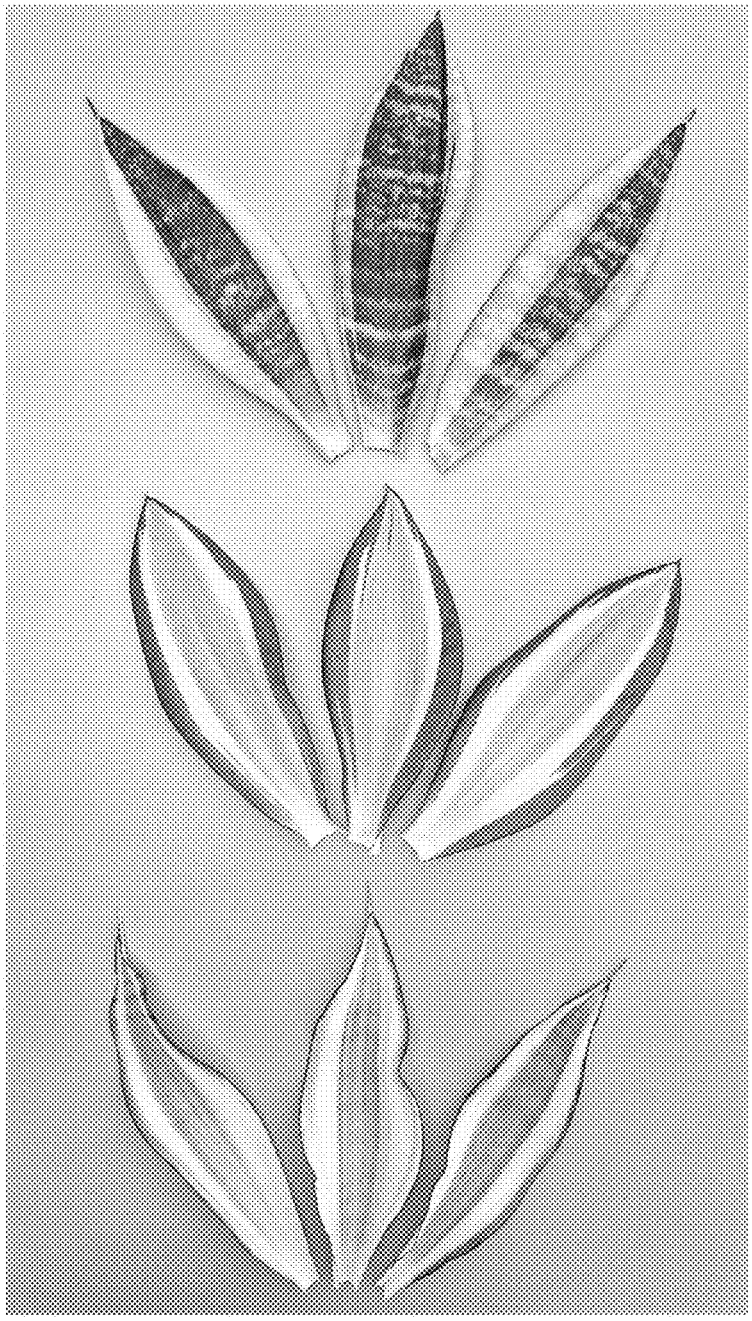
FIG. 9 shows individual leaves (adaxial surface) of *Sansevieria* 'Hansoti58' (Center), the parental variety 'Ghost' (Bottom row)—and leaves of *Sansevieria* 'Futura Superba' (Top Row) compared to show the differences in variegation pattern and colour.
Figure 10:
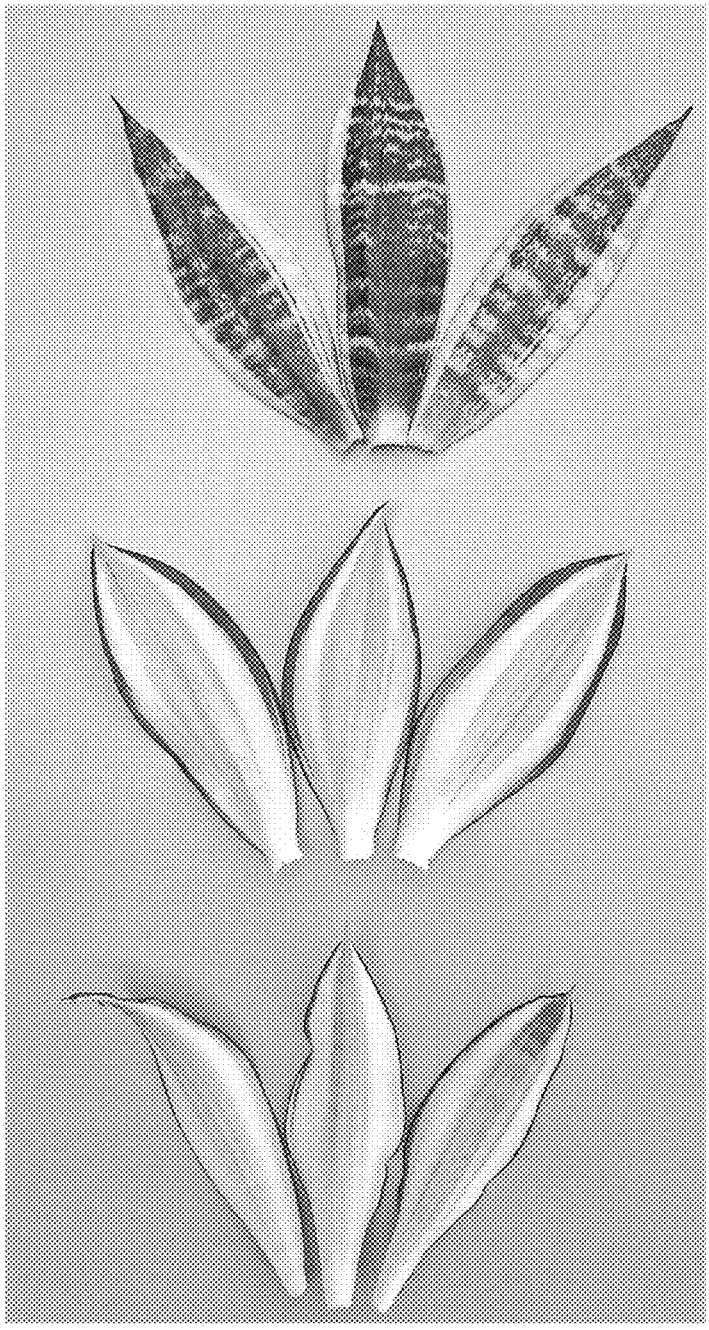
FIG. 10 shows individual leaves (abaxial surface) of *Sansevieria* 'Hansoti58' (Center), the parental variety 'Ghost' (Bottom row)—and leaves of *Sansevieria* 'Futura Superba' (Top Row).

The new *Sansevieria* 'HANSOTI58' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI58' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer of 13:11:11 Type 360-days release at 1 kilo/cubic meter of media, constant liquid feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the winter season in Asle, District Satara, Maharashtra State, India when outdoor day temperature was 25° C. to 30° C. and cool nights, usually of 10° C. to 15° C. The age of the plant described is 3-4 months from rooted liners.

Botanical classification: *Sansevieria trifasciata* 'HANSOTI58'.

General information:

*Parentage.*—*Sansevieria trifasciata* 'Ghost', unpatented.

*Optimal growth conditions.*—

*Light intensities.*—High adaptability to outdoor or indoor conditions but needs some shade in hot climates. Shade levels of 35% to 75% depending on season to give maximum light intensity of 350 to 500 $\mu mol/m^2/s$.

*Temperature.*—Day: 25° C. to 35° C. Night: 15° C. to 25° C.

*Temperature tolerance.*—Tolerant to a low temperature of about 6° C. and a high temperature of 38° C. and above — very heat tolerant.

*Fertilization.*—Constant feed of 100 ppm N, 20 ppm P and 100 ppm K is used along with micronutrients with occasional leaching. Nutricote 13:11:11 added at 1 kg/cubic meter of growing media.

*Growth regulators.*—Not necessary for growth, however rooting hormone aids in rapid and prolific rooting of offsets.

Propagation:

*Typical*.—Vegetative, by side suckers which consistently come true to type. Does not come true from leaf cuttings.

*Rooting habit and description*.—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots*.—25 to 30 days at 25° C. to 30° C.

*Time to produce a rooted liner*.—About 25 to 30 days at 25° C. to 30° C.

*Time to produce ready* 12 *cm potted plant from liner*.—About 12-15 weeks at 25° C. to 30° C.

Plant:

*General appearance and form*.—Monocot; leaf bases arranged in a rosette around growth point.

*Height*.—About 20 to 25 cm when grown in 12 cm pots.

*Spread*.—About 30 to 35 cm when grown when grown in a 12 cm size container.

*Growth rate and habit*.—Moderate; semi-upright.

*Shape*.—Inverted triangle.

*Fragrance*.—None.

*Stem*.—Modified (rhizomes with erect foliage).

*Rosette height*.—About 25 to 30 cm height from top of pot when grown in 12 cm size container.

*Rosette diameter*.—About 15 to 20 cm.

*Texture*.—Smooth, waxy.

*Color*.—As described above.

*Strength*.—Strong and durable.

*Internode length*.—About 1 to 2 mm.

Foliage:

*Quantity*.—About 5 to 7 leaves.

*Arrangement and attachment*.—Single, alternate; leaf bases arranged in a rosette around central growth point.

*Leaf length*.—About 20 to 25 cm.

*Leaf width*.—About 5 to 7 cm, occasionally a little more.

*Overall shape of leaf*.—Broad lanceolate.

*Apex shape*.—Acute, triangular and aristate, with soft tip.

*Base shape*.—Plane.

*Margin*.—Sharp, smooth.

*Texture*.—Upper Surface: Smooth and waxy texture.

*Texture*.—Under Surface: Smooth and waxy texture.

*Pubescence*.—None.

*Color of mature leaf*.—Upper Surface: Basal cream color (Between edge and central band) near RHS Yellow 4D with a central band varying from Green-Grey 188C or 188D to 189C or 189D—exact shade difficult to pinpoint because cream color overlays or veils the central green band.

*Margins*.—Darker grey-green close to RHS Green 138B.

*Crossbanding*.—As typical for many *Sansevieria trifasciata* but much less prominent, almost unnoticeable (noted above).

*Venation pattern*.—Longitudinal/parallel to leaf shape.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Occasionally shows *Anthracnose* and leaf spots but largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI58' as herein illustrated and described.

* * * * *